US00PP24829P3

(12) United States Plant Patent
Olesen

(10) Patent No.: US PP24,829 P3
(45) Date of Patent: Sep. 2, 2014

(54) COMPACT FLORIBUNDA ROSE PLANT NAMED 'POULCAS037'

(50) Latin Name: ***Rosa* hybrid**
Varietal Denomination: Poulcas037

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 42 days.

(21) Appl. No.: 13/507,006

(22) Filed: May 31, 2012

(65) Prior Publication Data

US 2013/0326762 P1 Dec. 5, 2013

(51) Int. Cl.
*A01H 5/00* (2006.01)

(52) U.S. Cl.
USPC ..... Plt./148

(58) Field of Classification Search
USPC ..... Plt./101, 141, 148
See application file for complete search history.

*Primary Examiner* — Susan McCormick Ewoldt

(57) ABSTRACT

A new garden rose plant of the Compact Floribunda class which has abundant, coral flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas037'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2003 and the resulting seeds were planted in a controlled environment in Fredensborg, Denmark. The new variety, named 'Poulcas037', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant coral flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas037' from all other varieties of which we are aware.

As part of the rose development program, Mogens N. Olesen germinated the seeds from the aforementioned hybridization during winter of 2003 and conducted evaluations on the resulting seedlings in a controlled environment in Fredensborg, Denmark. 'Poulcas037' was selected in the spring of 2004 by the inventor as a single plant from the progeny of the aforementioned hybridization.

Asexual reproduction of 'Poulcas037' by traditional budding and rooted cuttings was first done by Mogens N. Olesen in the nursery in Fredensborg, Denmark in July, 2004. This initial and other subsequent asexual propagations conducted in controlled environments have demonstrated that the characteristics of 'Poulcas037' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas037'.

Specifically illustrated in FIG. 1 are flowers at various stages of development, flower in parts, leaves, and stems.

Figure 1:
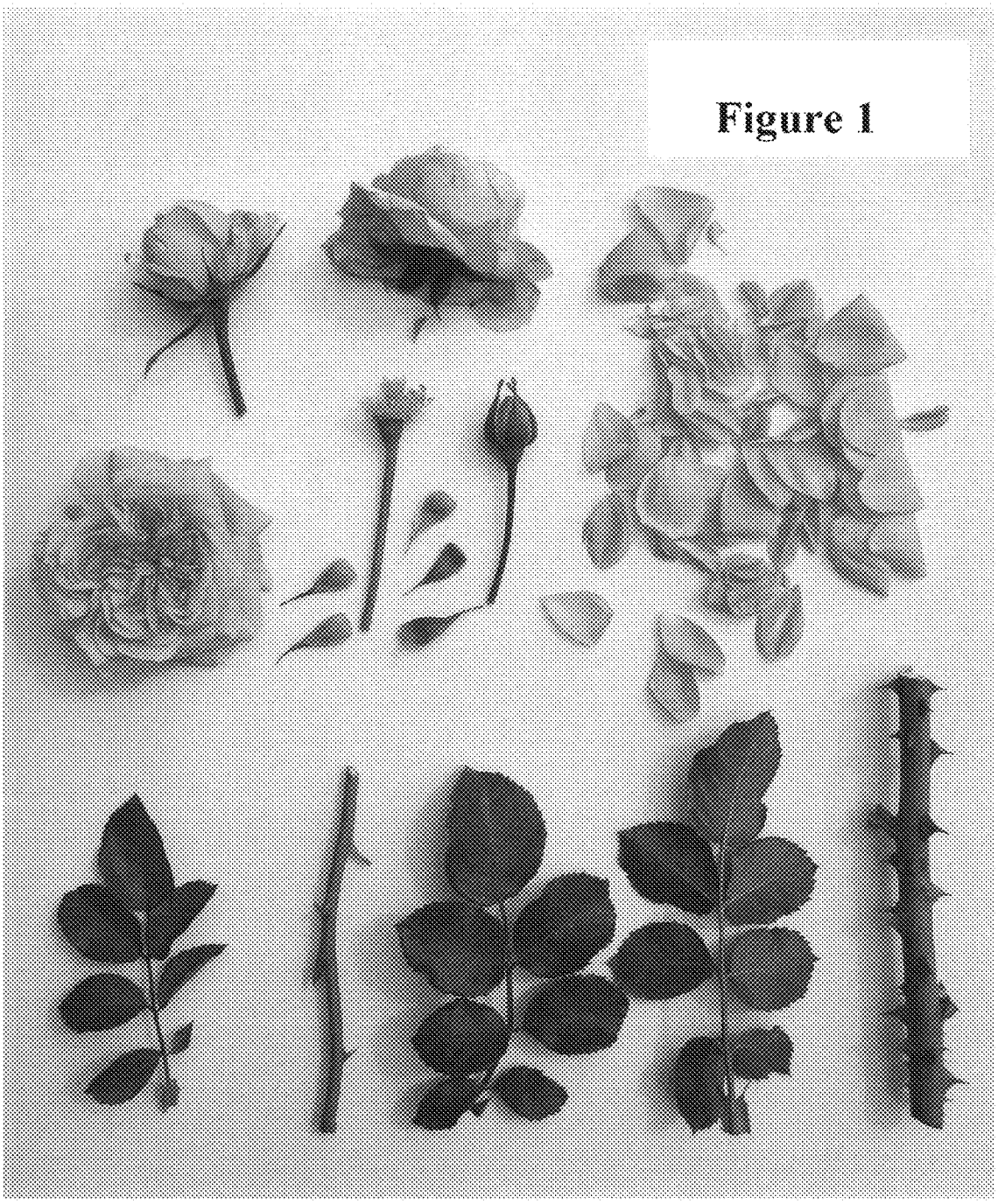
Figure 2:
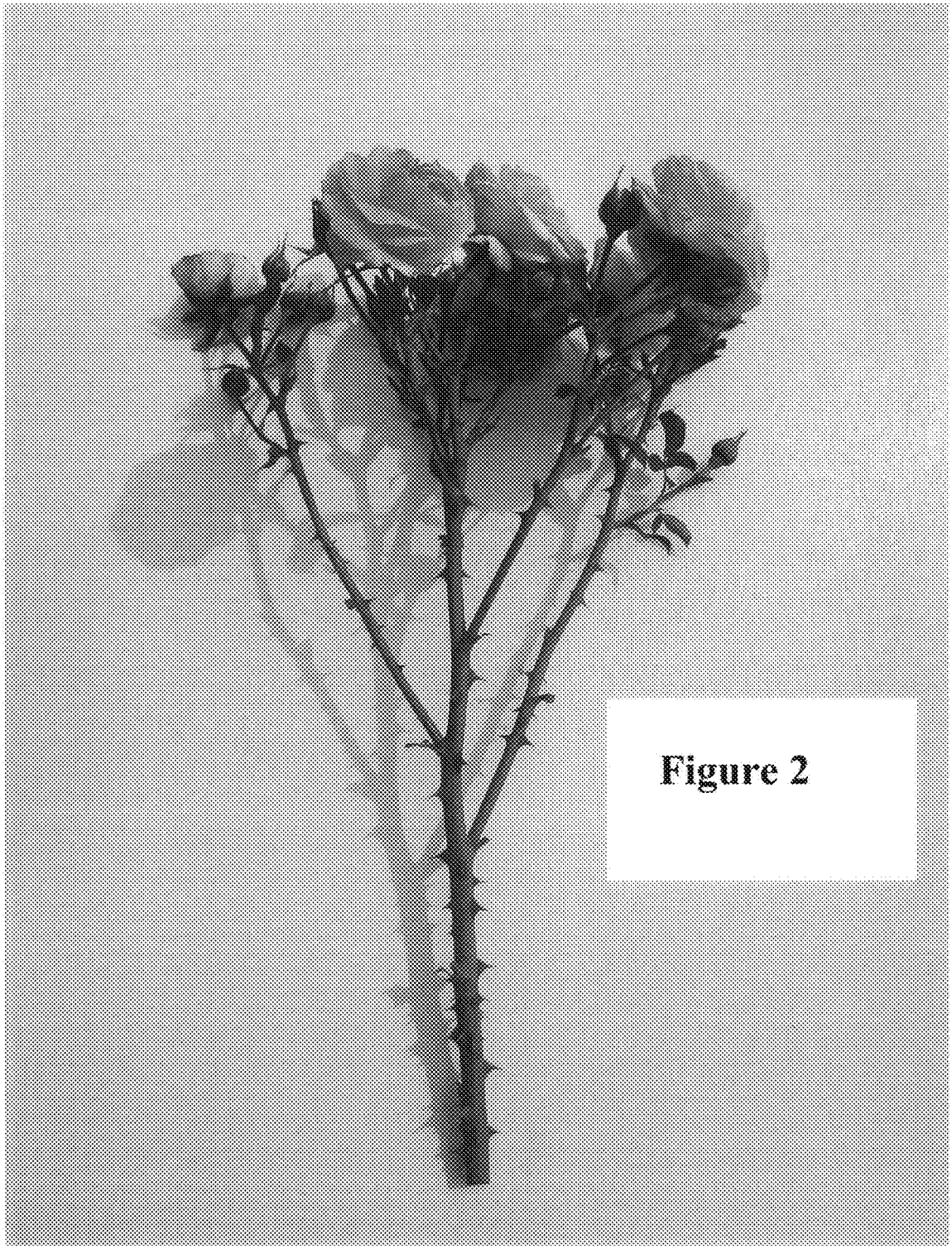
FIG. 2 illustrates the arrangement of peduncles and flowers on a flowering branch.

Plants shown in the drawings are 2 years of age.

DETAILED DESCRIPTION OF THE VARIETY

The following is a description of 'Poulcas037', as observed in its growth in in a field nursery in Marion County, Oreg. Observed plants are 3 years of age, and were grown on their own roots. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulcs011', U.S. Plant Pat. No. 15,232 are compared to 'Poulcas037' in Chart 1.

CHART 1

| | 'Poulcas037' | 'Poulcs011' |
|---|---|---|
| Petal Count | 125 petals, 15 of which are petaloids. | 35 petals under normal conditions with 9 petaloids |
| Flower Diameter | 65 to 70 mm | 60 to 70 mm |
| General Tonality of Flower Color | Red Group 43D with intonations of Orange Group 29C. | Orange Group 27A with intonations of Red Group 50D |

FLOWER AND FLOWER BUD

Blooming habit: Continuous.

Flower bud:

*Size*.—Upon opening, 21 mm in length from base of receptacle to end of bud. Bud diameter is 15 mm.

*Bud form*.—Urceolate.

*Bud color*.—As sepals divide petals are Orange Group 25A and Orange-Red Group 30B.

*Sepal inner surface*.—Color: Green Group 138B. Surface: Smooth and pubescent.

*Sepal outer surface*.—Color: Yellow-Green Group 144A with weak intonations of Greyed-Red Group 178B. Texture: Smooth.

*Sepal shape*.—Apex: Cirrhose. Base: Flat at union with receptacle.

*Sepal margin*.—Margins are absent of foliaceous appendages.

*Sepal size*.—25 mm long by 9 mm wide.

*Receptacle*.—Texture: Smooth. Size: 5 mm in height by 6 mm wide. Color: Yellow-Green Group 144B. Shape: Campanulate.

*Pedicel*.—Surface: Smooth. Length: 25 to 35 mm. Diameter: 3 mm on average. Color: Yellow-Green Group 144A with anthocyanic pigments the color of Greyed-Purple Group 187A. Strength: Moderately strong.

*Peduncle*.—Length: 20 to 30 cm. Diameter: 3 to 5 mm. Color: Yellow-Green Group 144A.

Flower bud development: Flower buds are borne in clusters of 5 flower buds per stem, resembling a panicle.

Flower bloom:

*Fragrance*.—None.

*Duration*.—The blooms have a duration on the plant of approximately 10 days. Petals fall cleanly away from plant after flowers have fully matured.

*Size*.—Flower diameter is 60 to 70 mm when open. Flower depth is 35 mm.

*Flower shape*.—General shape is a quartered rosette, very double, with many overlapping petals packed into quarter sections.

*Shape of flower, side view*.—Upon opening the upper portion is flat. The lower portion is concave.

Petalage: Under normal conditions, flowers have 125 petals, 15 of which are petaloids.

Petal color:

*Upon opening, outer petals*.—Upper surface: Red Group 41C. Lower surface: Red Group 41D splashed with intonations of Yellow Group 4D.

*Upon opening, inner petals*.—Upper surface: Orange Group 28A and Orange Red Group 32C. Lower surface: Red Group 41D and Orange Group 29C.

*Basal petal spots, upon opening*.—Upper surface: Yellow Group 6A. Lower surface: Yellow Group 4B.

*After opening, outer and inner petals*.—Upper surface: Red Group 49A. At the middle zone Orange Group 27A. Lower surface: Red Group 49A. At the middle zone Orange Group 27A.

*Basal petal spots, after opening*.—Upper surface: Yellow Group 6A. Lower surface: Yellow Group 4B.

General tonality: Open flowers are Red Group 43D with intonations of Orange Group 29C. Tonality changes to Red Group 52C as the flower ages.

Petals:

*Petal reflex*.—Outer petals are strongly reflexed.

*Margin*.—Entire and uniform. Weak undulations of margin observed.

*Shape*.—Generally narrow elliptic. Apex shape: Rounded. Base shape: Acute.

*Size*.—30 mm (l)×30 mm (w).

*Texture*.—Smooth.

*Thickness*.—Average.

Petaloids:

*Size*.—15 mm (l) by 10 mm (w).

*Quantity*.—15 on average.

*Shape*.—Apex is acute with a cleft at the margin. Base is acute. The petaloids are folded irregularly.

*Color*.—Orange Group 28A and Orange Red Group 32C with a petal spot of Yellow Group 6A, on upper surface. Lower surface is Red Group 41D and Orange Group 29C, with basal intonations of Yellow Group 4B.

Reproductive organs:

*Pollen*.—None observed.

*Anthers*.—Size: 2 mm in length. Color: Yellow Group 13A. Quantity: 35 on average.

*Filaments*.—Color: Yellow Group 7A. Length: 4 to 5 mm.

*Pistils*.—Length: 6 mm. Quantity: 30 on average.

*Stigmas*.—Color: Greyed-Yellow Group 160D. Location of stigmas: Superior in location relative to the length of the filaments and the height of the anthers.

*Styles*.—Color: Orange-White Group 159B.

*Hips*.—None Observed.

PLANT

Plant growth: Upright, bushy. Plants are 50 cm in height, and 50 cm wide.

Stems:

*Color*.—Juvenile growth: Yellow-Green Group 144A. Mature growth: Yellow-Green Group 144A.

*Length*.—On average, canes are 35 cm from the base of the plant to the flowering portion.

*Diameter*.—9 mm.

*Internodes*.—On mature canes, there is an average distance of 50 mm between nodes.

*Surface texture*.—Young wood: Smooth. Older wood: Mostly smooth with a few small prickles.

Long prickles:

*Incidence*.—20 prickles per 10 cm of stem.

*Size*.—Average length of prickles on mature stems is 10 mm.

*Shape*.—Upper portion is linear. Lower portion is concave.

*Color*.—Juvenile prickles: Greyed-Orange Group 166A. Mature prickles: Greyed-Yellow Group 160A.

Plant foliage:

*Compound leaf*.—110 mm (l)×75 (w).

*Quantity*.—2 leaves per 10 cm of stem on average.

*Color of juvenile foliage*.—Upper side: Yellow-Green Group 146A. Lower side: Yellow-Green Group 144A. Other intonations: Greyed-Red Group 178A at margins.

*Color of mature foliage*.—Upper side: Yellow-Green Group 146A. Lower side: Yellow-Green Group 146B.

Plant leaves and leaflets:

*Stipules*.—Size: 15 mm in length. Width is about 5 mm. Quantity: 2 per compound leaf. Shape: Linear, slightly broad based with outward extending apices. Margins: Finely serrated with few stipitate glands. Color: Yellow-Green Group 146B.

*Petiole*.—Length: 20 mm. Diameter: 2 mm.

*Upper surface*.—Color: Yellow-Green Group 144A.

*Lower surface*.—Color: Yellow-Green Group 144A.

*Rachis*.—Length: 60 mm.

*Upper surface*.—Color: Yellow-Green Group 144A.

*Lower surface*.—Color: Yellow-Green Group 144A.

*Leaflet*.—Quantity: Normal number of leaflets per leaf in middle of the stem is 7 leaflets. Margins: Serrated. Size: Average size of the terminal leaflet on normal leaves is 40 mm in length by 30 mm wide. Shape: Generally ovate. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Compact Floribunda rose class named 'Poulcas037', substantially as illustrated and described herein, due to its abundant coral flowers, disease resistance, and extended period of bloom.

* * * * *